United States Patent [19]

Ishihara et al.

[11] Patent Number: 5,580,893
[45] Date of Patent: Dec. 3, 1996

[54] NITROXYALKYLAMIDE DERIVATIVES

[75] Inventors: Sadao Ishihara; Fujio Saito; Mitsuru Kataoka; Hiroyuki Koike; Shigeki Miyake; Hiroshi Mizuno, all of Tokyo, Japan

[73] Assignee: Sankyo Company, Limited, Tokyo, Japan

[21] Appl. No.: 211,904

[22] PCT Filed: Nov. 2, 1992

[86] PCT No.: PCT/JP92/01419

§ 371 Date: Jul. 25, 1994

§ 102(e) Date: Jul. 25, 1994

[87] PCT Pub. No.: WO93/09085

PCT Pub. Date: May 13, 1993

[30] Foreign Application Priority Data

Nov. 7, 1991 [JP] Japan .................................. 3-291410

[51] Int. Cl.$^6$ .......................... A61K 31/41; C07D 261/06
[52] U.S. Cl. .......................... 514/378; 514/379; 514/438; 514/445; 514/446; 514/448; 514/452; 514/471; 514/617; 548/247; 548/248; 548/240; 548/241; 549/62; 549/65; 549/70; 549/72; 549/76; 549/362; 549/475; 549/479; 549/487; 549/495; 564/182; 564/183
[58] Field of Search ..................... 548/247, 248, 548/240, 241; 514/378, 379, 617, 438, 445, 446, 448, 471, 452; 564/182, 183; 549/62, 65, 70, 72, 76, 475, 479, 487, 495, 362

[56] References Cited

U.S. PATENT DOCUMENTS

| | | | |
|---|---|---|---|
| 4,200,640 | 4/1980 | Nagano et al. | 424/266 |
| 4,801,596 | 1/1989 | Simon et al. | 514/327 |
| 5,298,516 | 3/1994 | Ishihara et al. | 514/369 |
| 5,356,918 | 10/1994 | Ishihara et al. | 514/376 |

FOREIGN PATENT DOCUMENTS

| | | |
|---|---|---|
| 0300400 | 1/1989 | European Pat. Off. . |
| 359335 | 3/1990 | European Pat. Off. . |
| 61-148151 | 7/1986 | Japan . |
| 63-233962 | 9/1988 | Japan . |
| 2-134316 | 5/1990 | Japan . |
| WO93/01163 | 1/1993 | WIPO . |

OTHER PUBLICATIONS

CA 111:23505t Preparation ... disorders. Shiokawa et al., p. 616, 1989.
CA 116:46294r Antiasthmatic ... salts. Mori et al., pp. 316–317, 1992.
CA 117:26555u Thiazolidine derivatives. Bron et al., p. 718, 1992.
Chemical Abstracts, vol. 89, No. 1, 3 Jul. 1978, Columbus, Ohio, abstract No 6236r, H. Nagano et al, "N–(Hydroxyalkyl)pyridinecarboxamide nitrate esters" p. 534, col. 1 of JP-A-78 009 775 (Chugai Pharmaceutical Co., Ltd.).
Chemical Abstracts, vol. 98, No. 25, 20 Jun. 1993, Columbus Ohio, abstract No. 215485w, Kowa Co., "Benzopyran derivatives", p. 549, col. 2 of JP-A-57 275 (Kowa Co.).
Chemical Abstracts, vol. 106, No. 21, 25 May 1987, Columbus, Ohio, abstract No. 176137w, H. Nagano et al, "Synthesis of 4–nitro–and 5–nitro–N–(2–nitroxyethyl)nicotinamide", p. 705, col. 1, & Yakugaku Zasshi, vol. 106, No. 10, 1986, pp. 872–877.
Chemical Abstracts, vol. 114, No. 7, 18 Feb. 1991, Columbus, Ohio, abstract No. 61947h., M. Tsujimoto, "Preparation of pyridincarboxamido)alcohol esters with nitric acid as coronary vasodilators", p. 674, col. 2, of JP-A–02 207 072 (Sagami Chemical Research Centre).
Chemical Abstracts, vol. 111, No. 17, 23 Oct. 1989, Columbus, Ohio, abstract No. 153840j, Y Ito et al, "Preparation of 2–(pyrazine–2–carboxamido)ethyl, nitrate as a vasodilator", p. 729, col. 2 of JP-A–01 056 667 (Hokuriku Pharmaceutical Co. Ltd.).
Chemical Abstracts, vol. 108 No. 17, 25 Apr. 1988, Columbus, Ohio, abstract No. 150164u, H. Nagano et al, "Preparation of (nitroxyethyl)nicotinamide derivatives for treatment of angina pectoris", p. 714, col. 2 of JP-A–62 286 968 (Chugai Pharmaceutical Co., Ltd.).

Primary Examiner—Joseph K. McKane
Attorney, Agent, or Firm—Frishauf, Holtz, Goodman, Langer & Chick, P.C.

[57] ABSTRACT

Nitroxyalkylamide compounds having the formula: $R^1—(A)_n—CONH—B'—ONO_2$ wherein $R^1$ is an optionally substituted furyl, furyloxy, thienyl, thienyloxy, isoxazolyl, phenoxy, phenylthio or 1,4-dibenzodioxanyl, A is a $C_1$–$C_4$ alkylene group; B' is a $C_1$–$C_4$ alkylene group; and n is 0 or 1. The compounds of the present invention have a desirable vasodilator action for collateral vessels and an anti-anginal action, and are useful as therapeutic agents for treating angina pectoris.

80 Claims, No Drawings

NITROXYALKYLAMIDE DERIVATIVES

This application is a 371 of PCT/JP92/01419 filed Nov. 2, 1992.

TECHNICAL FIELD

The present invention relates to nitroxyalkylamide derivatives and pharmaceutically acceptable salts thereof having excellent vasodilator activity for the collateral vessels and anti-anginal action.

BACKGROUND ART

At present, nitroglycerin is most frequently used clinically as a therapeutic agent for cardiovascular diseases, particularly for angina pectoris.

This agent, however, has some faults such as being susceptible to undergoing the first-pass effect and having a short duration of action. Furthermore, side effects occur, such as headache and dizziness and tachycardia caused by hypotension. Against this background, therapeutic agents for angina pectoris which undergo no first-pass effect and have fewer side effects during clinical treatment have been desired.

Nitroxyalkylamide derivatives having anti-anginal action have been disclosed, for example, in U.S. Pat. No. 4200640 and Japan Kokai Hei 2-134316. However, in the latter Kokai, there is no specific description.

DISCLOSURE OF INVENTION

The present inventors have eagerly studied for many years the synthesis of nitroxy compounds and the pharmacological actions thereof.

As a result, they have found that compounds having a nitroxyalkylamide group have excellent vasodilator action on the collateral vessels, have fewer side effects and are useful as therapeutic agents for angina pectoris; they thus completed the present invention.

CONSTITUTION OF INVENTION

The present invention relates to nitroxyalkylamide derivatives having the general formula:

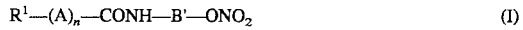

$$R^1-(A)_n-CONH-B'-ONO_2 \quad (I)$$

[in this formula, $R^1$ represents a 5- or 6-membered heterocyclic group (which may be optionally substituted or optionally condensed with a phenyl ring) containing from 1 to 3 hetero-atoms selected from the group consisting of nitrogen, oxygen and sulfur atoms; a 5- or 6-membered heterocyclic-oxy group (which may be optionally substituted or optionally condensed with a phenyl ring) containing from 1 to 3 hetero-atoms selected from the group consisting of nitrogen, oxygen and sulfur atoms; an optionally substituted $C_6-C_{10}$ aryloxy group; or an optionally substituted $C_6-C_{10}$ arylthio group (the substituents are selected from the group consisting of $C_1-C_4$ alkyl groups; $C_1-C_4$ alkoxy groups; phenyl groups optionally substituted with a $C_1-C_4$ alkyl group, with a $C_1-C_4$ alkoxy group, or with halogen atom(s); halogen atoms; hydroxy groups; amino groups; mono- or di-$C_1-C_4$ alkylamino groups; and nitro groups); A represents a $C_1-C_4$ alkylene group; B' represents a $C_1-C_4$ alkylene group; and n represents 0 or 1;

provided that, when n is 0, $R^1$ represents a 5- or 6-membered heterocyclic group (which may be optionally substituted or optionally condensed with a phenyl ring) containing from 1 to 2 hetero-atoms selected from the group consisting of oxygen and sulfur atoms; a 5- or 6-membered heterocyclic-oxy group (which may be optionally substituted or optionally condensed with a phenyl ring) containing from 1 to 3 hetero-atoms selected from the group consisting of nitrogen, oxygen and sulfur atoms; an optionally substituted $C_6-C_{10}$ aryloxy group; or an optionally substituted $C_6-C_{10}$ arylthio group]

or pharmaceutically acceptable salts thereof; a preventive and therapeutic agent for angina pectoris comprising the nitroxyalkylamide derivatives or pharmaceutically acceptable salts thereof mentioned above as an active ingredient: and preparation of the nitroxyalkylamide derivatives or pharmaceutically acceptable salts thereof mentioned above.

The 5- or 6-membered heterocyclic group (which may be optionally substituted or optionally condensed with a phenyl ring) containing from 1 to 3 hetero-atoms selected from the group consisting of nitrogen, oxygen and sulfur atoms; or the heterocyclic moiety in a 5- or 6-membered heterocyclic-oxy group (which may be optionally substituted or optionally condensed with a phenyl ring) containing from 1 to 3 hetero-atoms selected from the group consisting of nitrogen, oxygen and sulfur atoms, each represented by $R^1$, may be a saturated or unsaturated heterocyclic group and includes, for example, the tetrahydrofuryl, tetrahydrothienyl, tetrahydropyranyl, pyrrolidyl, piperidyl, imidazolidinyl, imidazolinyl, 1,4-dioxanyl, morpholinyl, thiomorpholinyl, piperazinyl, pyrrolinyl, furyl, thienyl, pyrrolyl, oxazolyl, oxadiazolyl, isoxazolyl, thiazolyl, thiadiazolyl, isothiazolyl, imidazolyl, pyrazolyl, triazolyl, pyranyl, pyridyl, pyridazinyl, pyrimidinyl, benzo-1,4-dioxanyl, indolyl, quinolyl or quinazolinyl group; preferably a 5- or 6-membered heterocyclic group containing from 1 to 2 hetero-atoms selected from the group consisting of nitrogen, oxygen and sulfur atoms; more preferably 1,4-dioxanyl, furyl, thienyl, oxazolyl, isoxazolyl, thiazolyl, isothiazolyl, pyridyl, pyridazinyl, pyrimidinyl or benzo-1,4-dioxanyl; still more preferably furyl, thienyl, oxazolyl, isoxazolyl, thiazolyl or benzo-1,4-dioxanyl; and particularly preferably furyl, thienyl, isoxazolyl or benzo-1,4-dioxanyl.

The aryl moiety in an optionally substituted $C_6-C_{10}$ aryloxy group or in an optionally substituted $C_6-C_{10}$ arylthio group, each represented by $R^1$, may be, for example a phenyl or naphthyl group; preferably a phenyl group.

The alkyl moiety in a $C_1-C_4$ alkyl group, in a $C_1-C_4$ alkoxy group or in a $C_1-C_4$ alkylamino group, each included in $R^1$, may be, for example a methyl, ethyl, propyl, isopropyl or butyl group; preferably a methyl or ethyl group; and particularly preferably a methyl group.

The halogen atom included in $R^1$, may be for example a fluorine, chlorine, bromine or iodine atom; preferably a fluorine, chlorine or bromine atom.

The $C_1-C_4$ alkylene group represented by A or B', may be, for example a methylene, ethylene, propylene, trimethylene or tetramethylene group; preferably a $C_1-C_2$ alkylene group for A, and a $C_2-C_3$ alkylene group (particularly $C_2$) for B'.

When compound (I) is basic, it can be converted into its pharmaceutically acceptable acid addition salts by any conventional means. As examples of such acid addition salts, there may be mentioned salts with a mineral acid such as hydrochloric acid, hydrobromic acid, sulfuric acid or phosphoric acid; salts with a carboxylic acid such as acetic acid, benzoic acid, oxalic acid, maleic acid, fumaric acid, tartaric acid or citric acid; and salts with a sulfonic acid such as methanesulfonic acid, benzenesulfonic acid or p-toluenesulfonic acid.

In addition, when asymmetric carbon atom(s) exist in the molecule of compound (I), the present invention includes its racemic and optical isomers.

Of the compounds having the general formula (I); preferred ones are:

1) Compounds where $R^1$ is a 5- or 6-membered heterocyclic group (which may be optionally substituted or optionally condensed with a phenyl ring) containing from 1 to 2 hetero-atoms selected from the group consisting of nitrogen, oxygen and sulfur atoms; a 5- or 6-membered heterocyclic-oxy group (which may be optionally substituted or optionally condensed with a phenyl ring) containing from 1 to 2 hetero-atoms selected from the group consisting of nitrogen, oxygen and sulfur atoms; an optionally substituted phenoxy group or an optionally substituted phenylthio group (the substituents are selected from the group consisting of $C_1$–$C_4$ alkyl groups, $C_1$–$C_2$ alkoxy groups, phenyl groups, halogen atoms, di-$C_1$–$C_2$ alkylamino groups and nitro groups);

2) Compounds where A is a $C_1$–$C_2$ alkylene group; and

3) Compounds where B' is a $C_2$–$C_3$ alkylene group (particularly a $C_2$ alkylene group).

More preferable ones are:

4) Compounds where $R^1$ is an optionally substituted furyl, furyloxy, thienyl, thienyloxy, isoxazolyl, isoxazolyloxy, phenoxy, phenylthio or 1,4-dibenzodioxanyl group (the substituents are selected from the group consisting of $C_1$–$C_2$ alkyl groups, phenyl, fluorine, chlorine, bromine, dimethylamino and nitro groups);

5) Compounds where A is a methylene or methylmethylene group; and

6) Compounds where B' is an ethylene group.

Particularly preferred ones are:

7) Compounds where $R^1$ is a phenoxy group and n is 0; or $R^1$ is a phenoxy group, a chlorophenoxy group, an optionally substituted isoxazol-3-yloxy group (the substituents are selected from the group consisting of methyl, phenyl, chlorine and bromine) or a 1,4-benzodioxanyl group, n is 1 and A is a methylene or methylmethylene group.

Preferable compounds represented by the general formula (I) can be exemplified specifically in Table 1.

TABLE 1

$R^1$-(A)$_n$-CONH-B$^1$-ONO$_2$ (I)

| Cpd. No. | $R^1$ | A | n | B$^1$ |
|---|---|---|---|---|
| 1 | PhO— | — | 0 | (CH$_2$)$_2$ |
| 2 | 2-Me—PhO— | — | 0 | (CH$_2$)$_2$ |
| 3 | 3-Me—PhO— | — | 0 | (CH$_2$)$_2$ |
| 4 | 4-Me—PhO— | — | 0 | (CH$_2$)$_2$ |
| 5 | 4-MeO-PhO— | — | 0 | (CH$_2$)$_2$ |
| 6 | 2-Cl—PhO— | — | 0 | (CH$_2$)$_2$ |
| 7 | 3-Cl—PhO— | — | 0 | (CH$_2$)$_2$ |
| 8 | 4-Cl—PhO— | — | 0 | (CH$_2$)$_2$ |
| 9 | PhO— | CH$_2$ | 1 | (CH$_2$)$_2$ |
| 10 | 2-Me—PhO— | CH$_2$ | 1 | (CH$_2$)$_2$ |
| 11 | 3-Me—PhO— | CH$_2$ | 1 | (CH$_2$)$_2$ |
| 12 | 4-Me—PhO— | CH$_2$ | 1 | (CH$_2$)$_2$ |
| 13 | 4-MeO-PhO— | CH$_2$ | 1 | (CH$_2$)$_2$ |
| 14 | 2-Cl—PhO— | CH$_2$ | 1 | (CH$_2$)$_2$ |
| 15 | 3-Cl—PhO— | CH$_2$ | 1 | (CH$_2$)$_2$ |
| 16 | 4-Cl—PhO— | CH$_2$ | 1 | (CH$_2$)$_2$ |

TABLE 1-continued $R^1$-(A)$_n$-CONH-B$^1$-ONO$_2$ (I)

| Cpd. No. | $R^1$ | A | n | B$^1$ |
|---|---|---|---|---|
| 17 | 2-NO$_2$—PhO— | CH$_2$ | 1 | (CH$_2$)$_2$ |
| 18 | 2-NO$_2$—PhO— | CH(Me) | 1 | (CH$_2$)$_2$ |
| 19 | PhO— | CH(Me) | 1 | (CH$_2$)$_2$ |
| 20 | PhO— | CH(Me) | 1 | (CH$_2$)$_2$ |
| 21 | PhO— | CH(Et) | 1 | (CH$_2$)$_2$ |
| 22 | PhO— | CH(Pr) | 1 | (CH$_2$)$_2$ |
| 23 | 2-Fur | — | 0 | (CH$_2$)$_2$ |
| 24 | 5-Br-2-Fur | — | 0 | (CH$_2$)$_2$ |
| 25 | 5-NO$_2$—2-Fur | — | 0 | (CH$_2$)$_2$ |
| 26 | 2-Thi | — | 0 | (CH$_2$)$_2$ |
| 27 | 3-Me-2-Thi | — | 0 | (CH$_2$)$_2$ |
| 28 | 5-Me-4-Cl-3-Isox—O— | CH$_2$ | 1 | (CH$_2$)$_2$ |
| 29 | 5-Ph-3-Isox—O— | CH$_2$ | 1 | (CH$_2$)$_2$ |
| 30 | 5-Me-3-Isox—O— | CH$_2$ | 1 | (CH$_2$)$_2$ |
| 31 | 5-Me-4-Br-3-Isox—O— | CH$_2$ | 1 | (CH$_2$)$_2$ |
| 32 | 3-Isox—O— | CH$_2$ | 1 | (CH$_2$)$_2$ |
| 33 | 5-Ph-4-Br-3-Isox—O— | CH$_2$ | 1 | (CH$_2$)$_2$ |
| 34 | 4-Br-3-Isox—O— | CH$_2$ | 1 | (CH$_2$)$_2$ |
| 35 | 5-Cl-3-Isox—O— | CH$_2$ | 1 | (CH$_2$)$_2$ |
| 36 | PhS— | CH$_2$ | 1 | (CH$_2$)$_2$ |
| 37 | 4-Cl—PhS— | CH$_2$ | 1 | (CH$_2$)$_2$ |
| 38 | 3-(Me$_2$N)-PhO— | CH$_2$ | 1 | (CH$_2$)$_2$ |
| 39 | 5-Ph-4-Cl-3-Isox—O— | CH$_2$ | 1 | (CH$_2$)$_2$ |
| 40 | 3-Fur | — | 0 | (CH$_2$)$_2$ |
| 41 | 3-Thi | — | 0 | (CH$_2$)$_2$ |
| 42 | 1,4-Bezdiox-2- | — | 0 | (CH$_2$)$_2$ |
| 43 | 2-Cl—PhO— | CH(Me) | 1 | (CH$_2$)$_2$ |
| 44 | 3-Cl—PhO— | CH(Me) | 1 | (CH$_2$)$_2$ |
| 45 | 4-Cl—PhO— | CH(Me) | 1 | (CH$_2$)$_2$ |
| 46 | PhO— | CH(iPr) | 1 | (CH$_2$)$_2$ |
| 47 | 4-Cl—PhO— | C(Me)$_2$ | 1 | (CH$_2$)$_2$ |
| 48 | 2-MeO—PhO— | CH$_2$ | 1 | (CH$_2$)$_2$ |
| 49 | 3-(Me$_2$N)-PhO— | CH$_2$ | 1 | (CH$_2$)$_2$ |
| 50 | 4-F—PhO— | CH$_2$ | 1 | (CH$_2$)$_2$ |
| 51 | 4-F—PhO— | CH(Me) | 1 | (CH$_2$)$_2$ |
| 52 | 3-Br—PhO— | CH$_2$ | 1 | (CH$_2$)$_2$ |
| 53 | 4-Br—PhO— | CH$_2$ | 1 | (CH$_2$)$_2$ |
| 54 | 4-Br—PhO— | CH(Me) | 1 | (CH$_2$)$_2$ |
| 55 | 4-(Me$_2$N)—PhO— | CH$_2$ | 1 | (CH$_2$)$_2$ |
| 56 | 4-(Me$_2$N)—PhO— | CH(Me) | 1 | (CH$_2$)$_2$ |
| 57 | 5-Ph-2-Fur | — | 0 | (CH$_2$)$_2$ |
| 58 | 5-Me-2-Fur— | — | 0 | (CH$_2$)$_2$ |
| 59 | 5-Cl-2-Fur— | — | 0 | (CH$_2$)$_2$ |
| 60 | 5-Ph-2-Thi— | — | 0 | (CH$_2$)$_2$ |
| 61 | 5-Br-2-Thi— | — | 0 | (CH$_2$)$_2$ |
| 62 | 5-Cl-2-Thi— | — | 0 | (CH$_2$)$_2$ |
| 63 | 5-Me-4-F-3-Isox—O— | CH$_2$ | 1 | (CH$_2$)$_2$ |
| 64 | 5-Me-4-Br-3-Isox—O— | CH$_2$ | 1 | (CH$_2$)$_2$ |
| 65 | 5-Me-4-F-3-Isox—O— | CH(Me) | 1 | (CH$_2$)$_2$ |
| 66 | 5-Me-4-Br—Isox—O— | CH(Me) | 1 | (CH$_2$)$_2$ |
| 67 | 5-Me-4-Cl-3-Isox—O— | CH(Me) | 1 | (CH$_2$)$_2$ |
| 68 | 5-Ph-4-F-3-Isox—O— | CH$_2$ | 1 | (CH$_2$)$_2$ |
| 69 | 5-Ph-4-Cl-3-Isox—O— | CH$_2$ | 1 | (CH$_2$)$_2$ |
| 70 | 5-Ph-4-F-3-Isox—O— | CH(Me) | 1 | (CH$_2$)$_2$ |
| 71 | 5-Ph-4-Br-3-Isox—O— | CH(Me) | 1 | (CH$_2$)$_2$ |
| 72 | 5-Ph-4-Cl-3-Isox—O— | CH(Me) | 1 | (CH$_2$)$_2$ |

In Table 1 above, abbreviations of groups are:

| Bezdiox: | Benzodioxanyl |
|---|---|
| Et: | Ethyl |
| Fur: | Furyl |
| Isox: | Isoxazolyl |
| Me: | Methyl |
| Ph: | Phenyl |
| Pr: | Propyl |
| Thi: | Thienyl. |

In Table 1 above, there may be mentioned as preferred compounds: Nos. 1, 2, 3, 4, 6, 8, 9, 11, 14, 15, 16, 19, 21, 23, 26, 28, 29, 30, 31, 32, 33, 34, 35, 36, 38, 39, 42, 43, 44, 45, 47, 63, 65, 66, 67 and 72; and as more preferred compounds, there may be mentioned:

Compound No. 1: Phenyl N-(2-nitroxyethyl) carbamate
Compound No. 9: N-(2-Nitroxyethyl)phenoxyacetamide
Compound No. 14: N-(2-Nitroxyethyl)-2-chlorophenoxyacetamide
Compound No. 19: N-(2-Nitroxyethyl)-2-phenoxypropanamide
Compound No. 28: N-(2-Nitroxyethyl)-5-methyl-4-chloro-3-isoxazolyloxyacetamide
Compound No. 29: N-(2-Nitroxyethyl)-5-phenyl-3-isoxazolyloxyacetamide
Compound No. 30: N-(2-Nitroxyethyl)-5-methyl-3-isoxazolyloxyacetamide
Compound No. 31: N-(2-Nitroxyethyl)-5-methyl-4-bromo-3-isoxazolyloxyacetamide
Compound No. 32: N-(2-Nitroxyethyl)-3-isoxazolyloxyacetamide
Compound No. 33: N-(2-Nitroxyethyl)-5-phenyl-4-bromo-3-isoxazolyloxyacetamide
Compound No. 34: N-(2-Nitroxyethyl)-4-bromo-3-isoxazolyloxyacetamide
Compound No. 35: N-(2-Nitroxyethyl)-4-chloro-3-isoxazolyloxyacetamide and
Compound No. 42: N-(2-Nitroxyethyl)-1,4-benzodioxane-2carboxamide.

Compounds having the general formula (I) of the present invention can easily be prepared by the following methods.

Method A

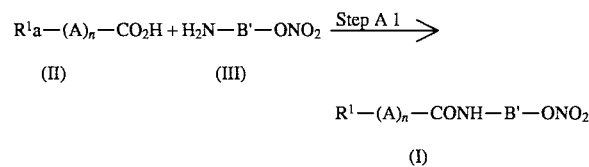

$$R^1a-(A)_n-CO_2H + H_2N-B'-ONO_2 \xrightarrow{\text{Step A 1}}$$
(II) \qquad (III)
$$R^1-(A)_n-CONH-B'-ONO_2$$
(I)

In the above formulae, $R^1$, A, B' and n have the same meanings as mentioned already and $R^1a$ represents the same meaning as $R^1$ except that the amino or monoalkylamino group in $R^1$ is optionally protected.

The amino- or monoalkylamino-protecting group is not particularly restricted provided that it is one of those commonly employed in the field of organic synthesis. For example, the t-butoxycarbonyl or a haloacetyl (such as chloroacetyl, bromoacetyl or iodoacetyl) groups may be mentioned.

Method A is for preparing Compound (I).

Step A1 is for preparing a compound having the general formula (I), and is carried out by reacting a compound having the general formula (II) or its reactive derivative with a compound having the general formula (III) in an inert solvent and then, if desired, by removing the amino- or monoalkylamino-protecting group. For example, the reaction is conducted by the acid halide method, the mixed acid anhydride method, the active ester method or the condensation method.

The acid halide method is conducted by reacting a compound having the general formula (II) with a halogenating agent and then reacting the resulting acid halide with a compound having the general formula (III) in an inert solvent and in the presence or absence of a base.

The base which may be employed may be, for example an organic amine such as triethylamine, N-methyl-morpholine or 4-dimethylaminopyridine; an alkali metal hydrogencarbonate such as sodium hydrogencarbonate or potassium hydrogencarbonate; or an alkali metal carbonate such as sodium carbonate or potassium carbonate; preferably an organic amine.

The inert solvent which may be employed is not particularly limited provided that it does not participate in the reaction, and it may be, for example a hydrocarbon such as hexane, cyclohexane, benzene, toluene or xylene; a halohydrocarbon such as dichloromethane, 1,2-dichloroethane or carbon tetrachloride; an ether such as diethyl ether, tetrahydrofuran or dioxane; a ketone such as acetone; an amide such as N,N-dimethylformamide, N,N-dimethyl-acetamide, N-methyl-2-pyrrolidone or hexamethyl-phosphoramide; or a sulfoxide such as dimethyl sulfoxide; preferably a hydrocarbon, a halohydrocarbon, an ether or an amide.

The reaction temperature varies depending on the starting compounds (II) and (III), and the kind of the solvent employed, but it is usually from −20° C. to 150° C. for both reactions of the halogenating agent with the Compound (II) and the acid halide with the Compound (III); preferably around room temperature for the reaction of the halogenating agent with the Compound (II) and from 0° C. to 100° C. for the reaction of the acid halide with the Compound (III). The reaction time varies depending on the reaction temperature etc., but it is from 30 minutes to 24 hours (preferably from 1 hour to 16 hours).

The mixed acid anhydride method is conducted by reacting a $C_1$–$C_4$ alkyl halocarbonate or a di-$C_1$–$C_4$ alkyl cyanophosphate with the Compound (II) and then by reacting the resulting acid anhydride with the Compound (III).

The reaction for preparing an acid anhydride is conducted by reacting a $C_1$–$C_4$ alkyl halocarbonate, such as ethyl chlorocarbonate or isobutyl chlorocarbonate, or a di-$C_1$–$C_4$ alkyl cyanophosphate, such as diethyl cyanophosphate, with the Compound (II). The reaction is preferably conducted in an inert solvent and in the presence of a base.

The base and inert solvent which may be employed are the same as those used in the acid halide method mentioned above.

The reaction temperature varies depending on the starting Compound (II) and the kind of solvent employed, but it is usually from −20° C. to 50° C. (preferably from 0° C. to 30° C.). The reaction time varies depending on the reaction temperature etc., but it is from 30 minutes to 24 hours (preferably from 1 hour to 16 hours).

The reaction of the resulting acid anhydride with the Compound (III) is preferably conducted in an inert solvent and in the presence or absence of a base. The base and inert solvent which may be employed are the same as those used in the acid halide method mentioned above.

The reaction temperature varies depending on the starting Compound (III) and the kind of solvent employed, but it is usually from −20° C. to 100° C. (preferably from 0° C. to near room temperature). The reaction time varies depending on the reaction temperature etc., but it is from 30 minutes to 24 hours (preferably from 1 hour to 16 hours).

On the other hand, by using the acid anhydride of Compound (II), which can be obtained from the Compound (II) and/or from any reactive derivative of the Compound (II), Compound (I) can be prepared using a similar reaction to that mentioned above. Compound (I) can be also prepared by the simultaneous presence of Compound (II) with Compound (III) in the presence of di-($C_1$–$C_4$)alkyl cyanophosphate.

The active ester method is conducted by reacting the Compound (II) directly with the Compound (III) in the presence of a condensation agent [for example, dicyclohexyl carbodiimide, carbonyldiimidazole or 1-(N,N-dimethylaminopropyl)-3-ethylcarbodiimide hydrochloride]. This reaction is conducted in a similar manner to that for preparing the active ester mentioned above.

After completion of the reaction, the desired product of the reaction can be recovered from the reaction mixture by conventional means. For example, the crystals which separated are collected by filtration; or, after addition of water, the reaction mixture is extracted with a water-immiscible organic solvent, such as ethyl acetate, and dried, and then the solvent is distilled off to obtain the desired compound. If necessary, it can be further purified by a conventional method, such as recrystallization or column chromatography.

Removal of the amino- or monoalkylamino-protecting group, which is conducted if desired, is carried out after the reaction above according to any conventional method commonly employed in the field of organic synthesis.

Where the protecting group is t-butoxycarbonyl, it can be removed by reacting a corresponding compound with an acid (for example, a mineral acid such as hydrochloric acid, sulfuric acid or nitric acid; or an organic acid such as acetic acid, trifluoroacetic acid, methanesulfonic acid or p-toluenesulfonic acid) in an inert solvent (for example, an ether such as diethyl ether, tetrahydrofuran or dioxane; a halohydrocarbon, such as dichloromethane or 1,2-dichloroethane; or an aromatic hydrocarbon, such as benzene, toluene or xylene) at from 0° C. to 50° C. (preferably at around room temperature) for from 30 minutes to 5 hours (preferably from 1 hour to 2 hours). Where the protecting group is a haloacetyl group, it can be removed by reacting a corresponding compound with thiourea in an inert solvent (for example, an amide such as dimethylformamide or dimethylacetamide; or a sulfoxide such as dimethyl sulfoxide) at from 0° C. to 50° C. (preferably at around room temperature) for from 30 minutes to 5 hours (preferably from 1 hour to 2 hours).

After completion of the reaction, the desired product of each reaction can be recovered from the reaction mixture by conventional means. For example, after neutralization of the reaction mixture, if necessary, the crystals which separated are collected by filtration; or, after addition of water, the reaction mixture is extracted with a water-immiscible organic solvent such as ethyl acetate and dried, and then the solvent is distilled off to obtain the desired compound. If necessary, it can be further purified by a conventional method such as recrystallization or column chromatography.

The starting compound (II) of Method A is known or is easily prepared by any known method [for example, J. Prakt. Chem., [2] 19, 396 (1879)].

Method B

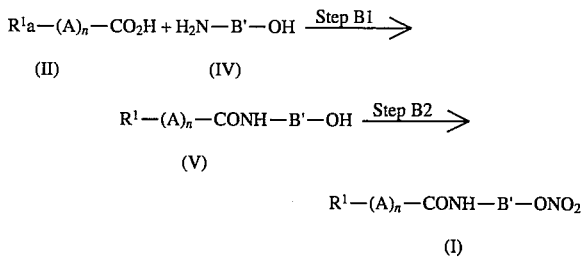

In the above formulae, $R^1$, $R^1a$ A, B' and n have the same meanings as mentioned already.

Method B is an alternative method for preparing a Compound (I).

Step B1 is for preparing a compound having the general formula (V), and is carried out by reacting a compound having the general formula (II) or its reactive derivative with a compound having the general formula (IV) in an inert solvent. For example, the reaction is conducted by the acid halide method, the mixed acid anhydride method, the active ester method or the condensation method in a similar manner to that in Step A 1.

Step B 2 is for preparing a compound having the general formula (I), and is carried out by reacting a compound having the general formula (V) with a nitrating agent in the presence or absence of an inert solvent.

The nitrating agent which may be employed may be, for example fuming nitric acid, nitrocollidinium tetrafluoroboron, thionyl chloride nitrate, thionyl nitrate or nitronium tetrafluoroboron; preferably fuming nitric acid, nitrocollidinium tetrafluoroboron or thionyl chloride nitrate.

The inert solvent which may be employed is not particularly limited provided that it does not participate in the reaction and it may be, for example, a hydrocarbon such as hexane, cyclohexane, benzene, toluene or xylene; a halohydrocarbon such as dichloromethane, 1,2-dichloroethane or carbon tetrachloride; an ether such as diethyl ether, tetrahydrofuran or dioxane; a ketone such as acetone; a polar solvent such as acetonitrile, N,N-dimethyl-formamide, N,N-dimethylacetamide, N-methyl-2-pyrrolidone, hexamethylphosphoramide or dimethyl sulfoxide; preferably a hydrocarbon, a halohydrocarbon, an ether or a polar solvent.

The reaction temperature varies depending on the starting compound (V) and the kind of nitrating agent employed, but is is usually from −20° C. to 50° C., preferably around room temperature. The reaction time varies depending on the reaction temperature etc., but it is from 30 minutes to 24 hours (preferably from 1 hour to 16 hours).

After completion of the reaction, the desired product of the reaction can be obtained from the reaction mixture by conventional means. For example, the crystals which separated are collected by filtration; or, after addition of water, the reaction mixture is extracted with a water-immiscible organic solvent such as ethyl acetate and dried, and then the solvent is distilled off to obtain the desired compound. If necessary, it can be further purified by a conventional method such as recrystallization or column chromatography.

Effect of Invention

Compounds having the general formula (I) of the present invention mentioned above exhibited a much stronger vasodilator activity for collateral vessels than nicorandil (U.S. Pat. No. 4,200,640) on tests carried out using the carotid collateral vessel system in an anesthesized dog. Therefore, the compounds are very useful as a preventive and therapeutic agent for angina pectoris.

TEST EXAMPLE 1

(Test method for vasodilator activity for collateral vessels)

Beagle dogs (male) weighing from 9 to 13 kg were anesthesized with 30 mg/kg of pentobarbital intravenously and the experiment was carried out under artificial respiration. To measure the left carotid artery pressure, a polyethylene cannula (atom venous catheter 2F) was inserted in a retrograde manner into one branch of the left thyroidal artery. The left carotid artery, upstream of the pressure measuring site, was occluded with an arterial forceps for one minute to measure the pressure immediately before the occlusion (P) and the pressure reduction in the peripheral vessels (ΔP). Next, a test sample was administered through a polyethylene canula which was inserted into the femoral vein, and the left carotid artery was occluded again for one minute after 5, 15, 30, 45 and 60 minutes, respectively, to measure the pressure immediately before the occlusion (P') and the pressure reduction in the peripheral vessels (ΔP'). The vasodilator activity for the collateral vessels (Collateral Index=CI) was determined by the following equation. Table 2 shows the result.

100−(ΔP'/P')×100/(ΔP/P)

TABLE 2

| Compound | CI (60)*⁾ (%), 0.1 mg/kg, iv |
| --- | --- |
| Compound of Example 1 | 31 |
| Compound of Example 20 | 36 |
| Compound of Example 23 | 19 |
| Compound of Example 26 | 21 |
| Compound of Example 32 | 20 |
| Compound of Example 35 | 20 |
| Nicorandil**⁾ | 7.2***⁾ |

*⁾The mean CI value during 60 minutes
**⁾The compound of U.S. Pat. No. 4200640
***⁾Intravenous administration at a dose of 0.3 mg/kg Possible exploitation in industry As mentioned above, the compounds having the formula (I) of the present invention have an excellent vasodilator activity for the collateral vessels and are very useful as preventive and therapeutic agents (in particular as a therapeutic agent) for angina pectoris.

When the Compound (I) is used as a therapeutic agent for angina pectoris, it can be administered orally or parenterally per se or as a pharmaceutical composition in the form of powders, granules, tablets, capsules, injections etc., which may be obtained by mixing the compound with a suitable pharmaceutically acceptable carrier, vehicle, diluent etc. The dosage varies depending on the nature of the disease to be treated and administration method, but it is usually from 1 mg to 1000 mg, preferably from 5 mg to 300 mg, for oral administration; and from 0.1 mg to 100 mg, preferably from 0.5 mg to 50 mg, for intravenous administration; and such a dose of the drug is desirably administered from 1 to 3 times a day depending on the conditions.

[The best mode for carrying out the invention]

The present invention will be described below more specifically by Examples but these examples do not limit the scope of the present invention.

EXAMPLE 1

Phenyl N-(2-nitroxyethyl)carbamate (Exemplified compound No. 1)

0.4 ml of triethylamine was added to a suspension of 0.5 g of diphenyl carbonate and 0.4 g of 2-nitroxyethylamine nitrate in 10 ml of acetonitrile. The mixture was stirred at room temperature for 2 hours and was then allowed to stand overnight at room temperature. The solvent was distilled off under reduced pressure, water was added to the residue, and it was extracted with ethyl acetate 3 times. The extracts were dried over magnesium sulfate and the solvent was distilled off under reduced pressure. The residue was purified by column chromatography through silica gel (eluent; hexane: ethyl acetate=5:1) to give 0.22 g of the title compound as colorless powdery crystals.

m.p.: 61°–62° C.

NMR spectrum (CDCl$_3$) δ ppm: 3.45–3.80 (2H, m), 4.60 (2H, t, J=6 Hz), 5.10–5.70 (1H, br.s), 7.00–7.50 (5H, m)

EXAMPLE 2

N-(2-Nitroxyethyl)phenoxyacetamide (Exemplified compound No. 9)

1.5 ml of triethylamine and 0.7 ml of diethyl cyanophosphate were added to a suspension of 0.65 g of phenoxyacetic acid and 0.6 g of 2-nitroxyethylamine nitrate in 20 ml of tetrahydrofuran with ice-cooling. The mixture was stirred at room temperature for 2 hours and the solvent was distilled off under reduced pressure. The residue was purified by column chromatography through silica gel (eluent; hexane: ethyl acetate=1:1) and then recrystallized from diisopropyl ether to give 0.27 g of the title compound as colorless needles.

m.p.: 61°–62° C.

NMR spectrum (CDCl$_3$) δ ppm: 3.58–3.82 (2H, m), 4.45–4.70 (4H, m), 6.80–7.50 (6H, m)

EXAMPLE 3

N-(2-Nitroxyethyl)-3-methylphenoxyacetamide (Exemplified compound No. 11)

Following a similar treatment to that in Example 2 and using 0.71 g of 3-methylphenoxyacetic acid and 0.6 g of 2-nitroxyethylamine nitrate, 0.50 g of the title compound was obtained as colorless powdery crystals (solvent for recrystallization; hexane).

m.p.: 40°–42° C.

NMR spectrum (DMSO-d$_6$) δ ppm: 2.29 (3H, s), 3.35–3.65 (2H, m), 4.47 (2H, s), 4.59 (2H, t, J=6 Hz), 6.70–7.30 (4H, m), 8.15–8.50 (1H, br.s)

EXAMPLE 4

N-(2-Nitroxyethyl)-2-chlorophenoxyacetamide (Exemplified compound No. 14)

Following a similar treatment to that in Example 2 and using 0.79 g of 2-chlorophenoxyacetic acid and 0.6 g of 2-nitroxyethylamine nitrate, 0.31 g of the title compound was obtained as colorless acicular prisms (solvent for recrystallization; diisopropyl ether).

m.p.: 57°–58° C.

NMR spectrum (DMSO-d$_6$) δ ppm: 3.42–3.65 (2H, m), 4.60 (2H, t, J=6 Hz), 4.63 (2H, s), 6.86–7.55 (4H, m), 8.00–8.40 (1H, br.s)

EXAMPLE 5

N-(2-Nitroxyethyl)-3-chlorophenoxyacetamide (Exemplified compound No. 15)

Following a similar treatment to that in Example 2 and using 0.79 g of 3-chlorophenoxyacetic acid and 0.6 g of 2-nitroxyethylamine nitrate, 0.28 g of the title compound was obtained as colorless needles (solvent for recrystallization; diisopropyl ether).

m.p.: 62°–64° C.

NMR spectrum (DMSO-d$_6$) δ ppm: 3.40–3.65 (2H, m), 4.57 (2H, s), 4.60 (2H, t, J=6 Hz), 6.85–7.48 (4H, m), 8.15–8.55 (1H, br.s)

EXAMPLE 6

N-1.2-Nitroxyethyl)-4-chlorophenoxyacetamide
(Exemplified compound No. 16)

Following a similar treatment to that in Example 2 and using 0.79 g of 4-chlorophenoxyacetic acid and 0.6 g of 2-nitroxyethylamine nitrate, 0.16 g of the title compound was obtained as colorless plates (solvent for recrystallization; diisopropyl ether).

m.p.: 86°–88° C.

NMR spectrum (DMSO-d$_6$) δ ppm: 3.38–3.65 (2H, m), 4.53 (2H, s), 4.60 (2H, t, J=6 Hz), 7.05 (2H, d, J=9 Hz), 7.35 (2H, d, J=9 Hz), 8.15–8.55 (1H, br.s)

EXAMPLE 7

N-(2-Nitroxyethyl)-2-(2-nitrophenoxy)propanamide
(Exemplified compound No. 18)

Following a similar treatment to that in Example 2 and using 0.75 g of 2-(2-nitrophenoxy)propionic acid and 0.6 g of 2-nitroxyethylamine nitrate, 0.45 g of the title compound was obtained as pale yellow needles (solvent for recrystallization; diisopropyl ether).

m.p.: 65°–67° C.

NMR spectrum (CDCl$_3$) δ ppm: 1.67 (3H, d, J=6 Hz), 3.55–3.85 (2H, m), 4.57 (2H, t, J=6 Hz), 4.97 (1H, q, J=6 Hz), 7.00–8.10 (5H, m)

EXAMPLE 8

N-(2-Nitroxyethyl)-2-(2-chlorophenoxy)propanamide
(Exemplified compound No. 43)

Following a similar treatment to that in Example 2 and using 0.71 g of 2-(2-chlorophenoxy)propionic acid and 0.6 g of 2-nitroxyethylamine nitrate, 0.43 g of the title compound was obtained as colorless needles (solvent for recrystallization; diisopropyl ether).

m.p.: 56°14 58° C.

NMR spectrum (CDCl$_3$) δ ppm: 1.63 (3H, d, J=6 Hz), 3.53–3.80 (2H, m), 4.57 (2H, t, J=6 Hz), 4.75 (1H, q, J=6 Hz), 6.85–7.52 (5H, m)

EXAMPLE 9

N-(2-Nitroxyethyl)-2-(3-chlorophenoxy)propanamide
(Exemplified compound No. 44)

Following a similar treatment to that in Example 2 and using 0.71 g of 2-(3-chlorophenoxy)propionic acid and 0.6 g of 2-nitroxyethylamine nitrate, 0.58 g of the title compound was obtained as colorless acicular prisms (solvent for recrystallization; diisopropyl ether).

m.p.: 67°–69° C.

NMR spectrum (CDCl$_3$) δ ppm: 1.57 (3H, d, J=6 Hz), 3.50–3.78 (2H, m), 4.53 (2H, t, J=6 Hz), 4.70 (1H, q, J=6 Hz), 6.70–7.40 (5H, m)

EXAMPLE 10

N-(2-Nitroxyethyl)-2-(4-chlorpophenoxy)propanamide
(Exemplified compound No. 45)

Following a similar treatment to that in Example 2 and using 0.71 g of 2-(4-chlorophenoxy)propionic acid and 0.60 g of 2-nitroxyethylamine nitrate, 0.51 g of the title compound was obtained as colorless needles (solvent for recrystallization; diisopropyl ether).

m.p.: 69°–71° C.

NMR spectrum (CDCl$_3$) δ ppm: 1.57 (3H, d, J=6 Hz), 3.50–3.80 (2H, m), 4.40–4.85 (3H, m), 6.70–7.45 (5H, m)

EXAMPLE 11

N-(2-Nitroxyethyl)-2-phenoxy-3-methylbutanamide
(Exemplified compound No. 46)

Following a similar treatment to that in Example 2 and using 0.47 g of 2-phenoxy-3-methylbutyric acid and 0.40 g of 2-nitroxyethylamine nitrate, 0.46 g of the title compound was obtained as colorless powdery crystals (solvent for recrystallization; diisopropyl ether).

m.p.: 76°–77° C.

NMR spectrum (CDCl$_3$) δ ppm: 1.08 (3H, d, J=6 Hz), 2.03–2.55 (1H, m), 3.47–3.73 (2H, m), 4.30–4.58 (3H, m), 6.60 (1H, br.s), 6.80–7.48 (5H, m)

EXAMPLE 12

N-(2-Nitroxyethyl)-2-phenoxypentanamide
(Exemplified compound No. 22)

Following a similar treatment to that in Example 2 and using 0.69 g of 2-phenoxyvaleric acid and 0.60 g of 2-nitroxyethylamine nitrate, 0.55 g of the title compound was obtained as colorless acicular prisms (solvent for recrystallization; diisopropyl ether).

m.p.: 68°–70° C.

NMR spectrum (CDCl$_3$) δ ppm: 0.80–2.10 (7H, m), 3.45–3.73 (2H, m), 4.30–4.70 (3H, m), 6.50–7.45 (6H, m)

EXAMPLE 13

N-(2-Nitroxyethyl)-2-phenoxybutanamide
(Exemplified compound No. 21)

Following a similar treatment to that in Example 2 and using 0.64 g of 2-phenoxybutyric acid and 0.60 g of 2-nitroxyethylamine nitrate, 0.55 g of the title compound was obtained as colorless acicular prisms (solvent for recrystallization; diisopropyl ether).

m.p.: 59°–61° C.

NMR spectrum (CDCl$_3$) δ ppm: 2.03 (3H, t, J=6 Hz), 1.78–2.20 (2H, m), 3.50–3.78 (2H, m), 4.35–4.70 (3H, m), 6.60–7.48 (6H, m)

EXAMPLE 14

N-(2-Nitroxyethyl)-2-phenoxypropanamide
(Exemplified compound No. 19)

Following a similar treatment to that in Example 2 and using 0.71 g of 2-phenoxypropionic acid and 0.60 g of 2-nitroxyethylamine nitrate, 0.49 g of the title compound was obtained as colorless needles (solvent for recrystallization; diisopropyl ether).

m.p.: 74°–75° C.

NMR spectrum (CDCl$_3$) δ ppm: 1.45 (3H, d, J=6 Hz), 3.25–3.63 (2H, m), 4.54 (2H, t, J=6 Hz), 4.70 (1H, q, J=6 Hz), 6.80–7.50 (5H, m), 8.08–8.55 (1H, br.s)

EXAMPLE 15

N-(2-Nitroxyethyl)phenylthioacetamide
(Exemplified compound No. 36)

Following a similar treatment to that in Example 2 and using 0.72 g of phenylthioacetic acid and 0.60 g of 2-nitroxyethylamine nitrate, 0.57 g of the title compound was obtained as colorless powdery crystals (solvent for recrystallization; diisopropyl ether).

m.p.: 63°–65° C.

NMR spectrum (DMSO-d$_6$) δ ppm: 3.30–3.52 (2H, m), 3.66 (2H, s), 4.50 (2H, t, J=6 Hz), 7.10–7.48 (5H, m), 8.20–8.55 (1H, br.s)

EXAMPLE 16

N-(2-Nitroxyethyl)-2-methyl-2-(4-chlorophenoxy)propanamide (Exemplified compound No. 47)

Following a similar treatment to that in Example 2 and using 0.91 g of 2-methyl-2-(4-chlorophenoxy)propionic acid and 0.60 g of nitroxyethylamine nitrate, 0.21 g of the title compound was obtained as colorless needles (solvent for recrystallization; diisopropyl ether).

m.p.: 81°–82° C.

NMR spectrum (CDCl$_3$) δ ppm: 1.50 (6H, s), 3.52–3.80 (2H, m), 4.57 (2H, t, J=6 Hz), 6.80–7.32 (5H, m)

EXAMPLE 17

N-(2-Nitroxyethyl)-2-methoxyphenoxyacetamide
(Exemplified compound No. 48)

Following a similar treatment to that in Example 2 and using 0.77 g of 2-methoxyphenoxyacetic acid and 0.60 g of nitroxyethylamine nitrate, 0.27 g of the title compound was obtained as colorless needles (solvent for recrystallization; diisopropyl ether).

m.p.: 63°–64° C.

NMR spectrum (CDCl$_3$) δ ppm: 3.55–3.80 (2H, m), 3.90 (3H, s), 4.48–4.68 (4H, m), 6.80–7.15 (4H, m), 7.25–7.75 (1H, br.s)

EXAMPLE 18

N-(2-Nitroxyethyl)-3-dimethylaminophenoxyacetamide
(Exemplified compound No. 38)

Following a similar treatment to that in Example 2 and using 0.83 g of 3-dimethylaminophenoxyacetic acid and 0.60 g of nitroxyethylamine nitrate, 0.50 g of the title compound was obtained as pale yellow acicular prisms (solvent for recrystallization; diisopropyl ether).

m.p.: 62°–63° C.

NMR spectrum (DMSO-d$_6$) δ ppm: 2.90 (6H, s), 3.40–3.70 (2H, m), 4.26 (2H, s), 4.60 (2H, t, J=6 Hz), 6.20–6.50 (3H, m), 6.95–7.25 (1H, m), 8.15–8.50 (1H, br.s)

EXAMPLE 19

N-(2-Nitroxyethyl)-5-methyl-3-isoxazolyloxyacetamide
(Exemplified compound No. 30)

Following a similar treatment to that in Example 2 and using 0.40 g of 5-methyl-3-isoxazolyloxyacetic acid and 0.43 g of nitroxyethylamine nitrate, 0.23 g of the title compound was obtained as colorless needles (solvent for recrystallization; diisopropyl ether).

m.p.: 93°–94° C.

NMR spectrum (CDCl$_3$) δ ppm: 2.37 (3H, s), 3.57–3.85 (2H, m), 4.60 (2H, t, J=6 Hz), 4.73 (2H, s), 5.73 (1H, s), 6.50–7.00 (1H, br.s)

EXAMPLE 20

N-(2-Nitroxyethyl)-5-methyl-4-chloroisoxazolyoxyacetamid (Exemplified compound No. 28)

Following a similar treatment to that in Example 2 and using 0.68 g of 5-methyl-4-chloro-3-isoxazolyloxyacetic acid and 0.60 g of nitroxyethylamine nitrate, 0.63 g of the title compound was obtained as colorless needles (solvent for recrystallization; diisopropyl ether).

m.p.: 88°–89° C.

NMR spectrum (CDCl$_3$) δ ppm: 2.37 (3H, s), 3.60–3.85 (2H, m), 4.60 (2H, t, J=6 Hz), 4.80 (2H, s), 6.40–6.90 (1H, br.s)

EXAMPLE 21

N-(2-Nitroxyethyl)-5-phenyl-3-isoxazolyloxyacetamide
(Exemplified compound No. 29)

Following a similar treatment to that in Example 2 and using 0.78 g of 5-phenyl-3-isoxazolyloxyacetic acid and 0.60 g of nitroxyethylamine nitrate, 0.58 g of the title compound was obtained as colorless needles (solvent for recrystallization; diisopropyl ether).

m.p.: 113°–114° C.

NMR spectrum (CDCl$_3$) δ ppm: 3.60–3.85 (2H, m), 4.60 (2H, t, J=6 Hz), 4.83 (2H, s), 6.25 (1H, s), 6.55–7.00 (1H, br.s), 7.35–7.85 (1H, m)

EXAMPLE 22

N-(2-Nitroxethyl)-4-Chloro-3-isoxazolyloxyacetamide
(Exemplified compound No. 35)

Following a similar treatment to that in Example 2 and using 0.43 g of 4-chloro-3-isoxazolyloxyacetic acid and 0.41 g of nitroxyethylamine nitrate, 0.21 g of the title compound was obtained as colorless needles (solvent for recrystallization; diisopropyl ether).

m.p.: 88°–89° C.

NMR spectrum (CDCl$_3$) δ ppm: 3.55–3.83 (2H, m), 4.58 (2H, t, J=6 Hz), 4.80 (2H, s), 6.50–7.00 (1H, br.s), 8.23 (1H, s)

EXAMPLE 23

N-(2-Nitroxyethyl)-4-bromo-3-isoxazoyloxyacetamide
(Exemplified compound No. 34)

Following a similar treatment to that in Example 2 and using 0.78 g of 4-bromo-3-isoxazolyloxyacetic acid and 0.60 g of nitroxyethylamine nitrate, 0.44 g of the title compound was obtained as colorless needles (solvent for recrystallization; diisopropyl ether).

m.p.: 98°–99° C.

NMR spectrum (CDCl$_3$) δ ppm: 3.60–3.88 (2H, m), 4.61 (2H, t, J=6 Hz), 4.83 (2H, s), 6.50–7.00 (1H, br.s), 8.26 (1H, s)

EXAMPLE 24

N-(2-Nitroxyethyl)-5-phenyl-4-chloro-3-isoxazolyl-oxyacetamide (Exemplified compound No. 39)

Following a similar treatment to that in Example 2 and using 0.70 g of 5-phenyl-4-chloro-3-isoxazolyloxyacetic acid and 0.46 g of nitroxyethylamine nitrate, 0.42 g of the title compound was obtained as colorless needles (solvent for recrystallization; diisopropyl ether).

m.p.: 138°–139° C.

NMR spectrum (CDCl$_3$) δ ppm: 3.60–3.90 (2H, m), 4.62 (2H, t, J=6 Hz), 4.87 (2H, s), 6.60–7.00 (1H, br.s), 7.40–8.10 (5H, m)

EXAMPLE 25

N-(2-Nitroxyethyl)-5-methyl-4-bromo-3-isoxazolyl-oxyacetamide (Exemplified compound No. 31)

Following a similar treatment to that in Example 2 and using 472 mg of 5-methyl-4-bromo-3-isoxazolyloxyacetic acid and 338 mg of nitroxyethylamine nitrate, 265 mg of the title compound was obtained as colorless needles (solvent for recrystallization; diisopropyl ether).

m.p.: 87°–88° C.

NMR spectrum (CDCl$_3$) δ ppm: 2.38 (3H, s), 3.73 (2H, dd, J=6, 11 Hz), 4.61 (2H, t, J=6 Hz), 4.79 (2H, s), 6.68 (1H, br.s)

EXAMPLE 36

N-(2-Nitroxyethyl)-3-isoxazolyloxyacetamide (Exemplified compound No. 32)

Following a similar treatment to that in Example 2 and using 286 mg of 3-isoxazolyloxyacetic acid and 338 mg of nitroxyethylamine nitrate, 250 mg of the title compound was obtained as colorless needles (solvent for recrystallization; diisopropyl ether).

m.p.: 67°–69° C.

NMR spectrum (CDCl$_3$) δ ppm: 3.72 (2H, dd, J=6, 11 Hz), 4.60 (2H, t, J=6 Hz), 4.79 (2H, s), 6.08 (1H, d, J=2 Hz), 6.71 (1H, br.s), 8.20 (1H, d, J=2 Hz)

EXAMPLE 27

N-(2-Nitroxyethyl)-3-furancarboxamide (Exemplified compound No. 40)

Following a similar treatment to that in Example 2 and using 0.48 g of 3-furancarboxylic acid and 0.60 g of nitroxy-ethylamine nitrate, 0.30 g of the title compound was obtained as colorless plates (solvent for recrystallization; diisopropyl ether).

m.p.: 80°–82° C.

NMR spectrum (CDCl$_3$) δ ppm: 3.73 (2H, dd, J=6, 11 Hz), 4.63 (2H, t, J=6 Hz), 6.52 (1H, br.s), 6.69 (1H, s), 7.46 (1H, s), 8.00 (1H, s)

EXAMPLE 28

N-(2-Nitroxyethyl)-3-thiophenecarboxamide (Exemplified compound No. 41)

Following a similar treatment to that in Example 2 and using 0.55 g of 3-thiophenecarboxylic acid and 0.60 g of nitroxyethylamine nitrate, 0.27 g of the title compound was obtained as colorless plates (solvent for recrystallization; diisopropyl ether).

m.p.: 100°–102° C.

NMR spectrum (DMSO-d$_6$) δ ppm: 3.60 (2H, dd, J=6, 11 Hz), 4.67 (2H, t, J=6 Hz), 7.40–7.68 (2H, m), 8.16 (1H, m), 8.40–8.65 (1H, br.s)

EXAMPLE 29

N-(2-Nitroxyethyl)-5-bromo-2-furancarboxamide (Exemplified compound No. 24)

Following a similar treatment to that in Example 2 and using 0.68 g of 5-bromo-2-furancarboxylic acid and 0.60 g of nitroxyethylamine nitrate, 0.22 g of the title compound was obtained as pale yellow acicular prisms (solvent for recrystallization; diisopropyl ether).

m.p.: 61°–63° C.

NMR spectrum (CDCl$_3$) δ ppm: 3.77 (2H, dd, J=6, 11 Hz), 4.63 (2H, t, J=6 Hz), 6.46 (1H, d, J=4 Hz), 6.63 (1H, br.s), 7.10 (1H, d, J=4 Hz)

EXAMPLE 30

N-(2-Nitroxyethyl)-5-nitro-2-furancarboxamide (Exemplified compound No. 25)

Following a similar treatment to that in Example 2 and using 0.56 g of 5-nitro-2-furancarboxylic acid and 0.60 g of nitroxyethylamine nitrate, 0.25 g of the title compound was obtained as yellow plates (solvent for recrystallization; diisopropyl ether).

m.p.: 102°–104° C.

NMR spectrum (CDCl$_3$) δ ppm: 3.83 (2H, dd, J=6, 11 Hz), 4.67 (2H, t, J=6 Hz), 7.00 (1H, br.s), 7.20–7.48 (2H, m)

EXAMPLE 31

N-(2-Nitroxyethyl)-3-methyl-2-thiophenecarboxamide (Exemplified compound No. 27)

Following a similar treatment to that in Example 2 and using 0.60 g of 3-methyl-2-thiophenecarboxylic acid and 0.60 g of nitroxyethylamine nitrate, 0.35 g of the title compound was obtained as colorless needles (solvent for recrystallization; diisopropyl ether).

m.p.: 74°–76° C.

NMR spectrum (DMSO-d$_6$) δ ppm: 2.42 (3H, s), 3.63 (2H, dd, J=6, 11 Hz), 4.67 (2H, t, J=6 Hz), 6.97 (1H, d, J=5 Hz), 7.59 (1H, d, J=5 Hz), 8.13 (1H, br.s)

EXAMPLE 32

N-(2-Nitroxyethyl)-1,4-benzodioxane-2-carboxamide (Exemplified compound No. 42)

Following a similar treatment to that in Example 2 and using 0.91 g of 1,4-benzodioxane-2-carboxylic acid and 0.85 g of nitroxyethylamine nitrate, 0.45 g of the title compound was obtained as colorless needles (solvent for recrystallization; diisopropyl ether).

m.p.: 69°–71° C.

NMR spectrum (CDCl$_3$) δ ppm: 3.55–3.83 (2H, m), 4.07–4.35 (1H, m), 4.45–4.86 (4H, m), 6.60–7.25 (5H, br.s)

EXAMPLE 33

N-(2-Nitroxyethyl)-2-furancarboxamide
(Exemplified compound No. 23)

Following a similar treatment to that in Example 2, using 0.34 g of 2-furancarboxylic acid and 0.50 g of nitroxyethylamine nitrate and using diphenylphosphoryl azide instead of ethyl cyanophosphate, 0.35 g of the title compound was obtained as colorless needles (solvent for recrystallization; diisopropyl ether).

m.p.: 88°–89° C.

NMR spectrum (DMSO-d$_6$) δ ppm: 3.57 (2H, dd, J=6, 11 Hz), 4.63 (2H, t, J=6 Hz), 6.67 (1H, m), 7.13 (1H, d, J=4 Hz), 7.87 (1H, s), 8.60 (1H, br.s)

EXAMPLE 34

N-(2-Nitroxyethyl)-2-thiophenecarboxamide
(Exemplified compound No. 26)

Following a similar treatment to that in Example 33 and using 0.38 g of 2-thiophenecarboxylic acid and 0.50 g of nitroxyethylamine nitrate, 0.27 g of the title compound was obtained as colorless plates (solvent for recrystallization; diisopropyl ether).

m.p.: 102°–103° C.

NMR spectrum (DMSO-d$_6$) δ ppm: 3.60 (2H, dd, J=6, 11 Hz), 4.66 (2H, t, J=6 Hz), 7.10–7.30 (1H, m), 7.70–7.88 (1H, m), 8.70 (1H, br.s)

EXAMPLE 35

N-(2-Nitroxyethyl)-5-phenyl-4-bromo-3-isoxazolyl-oxyacetamide (Exemplified compound No. 33 )

Following a similar treatment to that in Example 2 and using 0.53 g of 5-phenyl-4-bromo-3-isoxazolyloxyacetic acid and 0.30 g of nitroxyethylamine nitrate, 0.44 g of the title compound was obtained as colorless needles (solvent for recrystallization; ethanol).

m.p.: 145°–146° C.

NMR spectrum (DMSO-d$_6$) δ ppm: 3.30–3.65 (2H, m), 4.60 (2H, t, J=6 Hz), 4.82 (2H, s), 7.50–7.73 (3H, m), 7.85–8.13 (2H, m), 8.20–8.70 (1H, br.s)

We claim:

1. A nitroxyalkylamide compound having the formula:

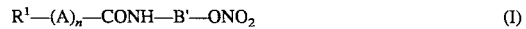

$$R^1-(A)_n-CONH-B'-ONO_2 \quad (I)$$

wherein $R^1$ is a furyl, furyloxy, thienyl, thienyloxy, isoxazolyl, isoxazolyloxy, phenoxy, phenylthio or 1,4-dibenzodioxanyl group, which is unsubstituted or substituted by a substituent selected from the group consisting of a $C_1$–$C_2$ alkyl group, phenyl, fluorine, chlorine, bromine, dimethylamino and nitro;

A is a $C_1$–$C_4$ alkylene group;

B' is a $C_1$–$C_4$ alkylene group; and n is 0 or 1;

or a pharmaceutically acceptable salt thereof.

2. The compound according to claim 1 in which A is a $C_1$–$C_2$ alkylene group.

3. The compound according to claim 1 in which B' is a $C_2$–$C_3$ alkylene group.

4. The compound according to claim 1 in which A is a methylene or methylmethylene group.

5. The compound according to claim 1 in which B' is an ethylene group.

6. The compound according to claim 1 in which A is a methylene or methylmethylene group; and B' is an ethylene group.

7. The compound according to claim 1 in which $R^1$ is a phenoxy group and n is 0; or $R^1$ is a phenoxy group, a chlorophenoxy group, an unsubstituted isoxazol-3-yloxy group, an isoxazol-3-yloxy group substituted by a substituent selected from the group consisting of methyl, phenyl, chlorine and bromine or a 1,4-benzodioxanyl group, n is 1, A is a methylene or methylmethylene group.

8. The compound according to claim 1 in which $R^1$ is a phenoxy group and n is 0; or $R^1$ is a phenoxy group, a chlorophenoxy group, an unsubstituted isoxazol-3-yloxy group, an isoxazol-3-yloxy group substituted by a substituent selected from the group consisting of methyl, phenyl, chlorine and bromine or a 1,4-benzodioxanyl group, n is 1, A is a methylene or methylmethylene group and B' is an ethylene group.

9. Phenyl N-(2-nitroxyethyl)carbamate according to claim 1.

10. N-(2-Nitroxyethyl)phenoxyacetamide according to claim 1.

11. N-(2-Nitroxyethyl)-2-chlorophenoxyacetamide according to claim 1.

12. N-(2-Nitroxyethyl)-2-phenoxypropanamide according to claim 1.

13. N-(2-Nitroxyethyl)-5-methyl-4-chloro-3-isoxazolyloxyacetamide according to claim 1.

14. N-(2-Nitroxyethyl-5-phenyl-3-isoxazolyloxyacetamide according to claim 1.

15. N-(2-Nitroxyethyl)-5-methyl-3-isoxazolyloxyacetamide according to claim 1.

16. N-(2-Nitroxyethyl)-5-methyl-4-bromo-3-isoxazolyloxyacetamide according to claim 1.

17. N-(2-Nitroxyethyl)-3-isoxazolyloxyacetamide according to claim 1.

18. N-(2-Nitroxyethyl)-5-phenyl-4-bromo-3-isoxazolyloxyacetamide according to claim 1.

19. N-(2-Nitroxyethyl)-4-bromo-3-isoxazolyloxyacetamide according to claim 1.

20. N-(2-Nitroxyethyl)-4-chloro-3-isoxazolyloxyacetamide according to claim 1.

21. N-(2-Nitroxyethyl)-1,4-benzodioxane-2-carboxamide according to claim 1.

22. An agent for preventing or treating angina pectoris comprising an effective amount of the nitroxyalkylamide compound according to claim 1 or pharmaceutically acceptable salt thereof, in combination with a pharmaceutically acceptable carrier.

23. The preventive and therapeutic agent for angina pectoris according to claim 22 in which A is a $C_1$–$C_2$ alkylene group.

24. The preventive and therapeutic agent for angina pectoris according to claim 22 in which B' is a $C_2$–$C_3$ alkylene group.

25. The preventive and therapeutic agent for angina pectoris according to claim 22 in which A is a methylene or methylmethylene group.

26. The preventive and therapeutic agent for angina pectoris according to claim 22 in which B' is an ethylene group.

27. The preventive and therapeutic agent for angina pectoris according to claim 22 in which A is a methylene or methylmethylene group and B' is an ethylene group.

28. The preventive and therapeutic agent for angina pectoris according to claim 22 in which $R^1$ is a phenoxy group and n is 0; or $R^1$ is a phenoxy group, a chlorophenoxy group, an unsubstituted isoxazol-3-yloxy group, an isoxazol-3-yloxy group substituted by a substituent selected from the group consisting of methyl, phenyl, chlorine and bromine or a 1,4-benzodioxanyl group, n is 1 and A is a methylene or methylmethylene.

29. The preventive and therapeutic agent for angina pectoris according to claim 22 in which $R^1$ is a phenoxy group and n is 0; or $R^1$ is a phenoxy group, a chlorophenoxy group, an unsubstituted isoxazol-3-yloxy group, an isoxazol-3-yloxy group substituted by a substituent selected from the group consisting of methyl, phenyl, chlorine and bromine or a 1,4-benzodioxanyl group, n is 1, A is a methylene or methylmethylene group and B' is an ethylene group.

30. A preventive and therapeutic agent for angina pectoris according to claim 22 in which the active ingredient is selected from the group consisting of phenyl N-(2-nitroxyethyl)carbamate,
N-(2-nitroxyethyl)phenoxyacetamide,
N-(2-nitroxyethyl)-2-chlorophenoxyacetamide,
N-(2-nitroxyethyl)-2-phenoxypropanamide,
N-(2-nitroxyethyl)-5-methyl-4-chloro-3-isoxazolyloxyacetamide,
N-(2-nitroxyethyl)-5-phenyl-3-isoxazolyloxyacetamide,
N-(2-nitroxyethyl)-5-methyl-3-isoxazolyloxyacetamide,
N-(2-nitroxyethyl)-5-methyl-4-bromo-3-isoxazolyloxyacetamide,
N-(2-nitroxyethyl)-3-isoxazolyloxyacetamide,
N-(2-nitroxyethyl)-5-phenyl-4-bromo-3-isoxazolyloxyacetamide,
N-(2-nitroxyethyl)-4-bromo-3-isoxazolyloxyacetamide,
N-(2-nitroxyethyl)-4-chloro-3-isoxazolyloxyacetamide and
N-(2-nitroxyethyl)-1,4-benzodioxane-2-carboxamide.

31. A method for preventing or treating angina pectoris in a patient in need thereof comprising administering to the patient an effective pharmaceutical amount of the compound according to claim 1 or a pharmaceutically acceptable salt thereof.

32. The method according to claim 31, wherein the compound is selected from the group consisting of phenyl N-(2-nitroxyethyl)carbamate,
N-(2-nitroxyethyl)phenoxyacetamide,
N-(2-nitroxyethyl)-2-chlorophenoxycetamide,
N-(2-nitroxyethyl)-2-phenoxypropanamide,
N-(2-nitroxyethyl)-5-methyl-4-chloro-3-isoxazolyloxyacetamide,
N-(2-nitroxyethyl)-5-phenyl-3-isoxazolyloxyacetamide,
N-(2-nitroxyethyl)-5-methyl-3-isoxazolyloxyacetamide,
N-(2-nitroxyethyl)-5-methyl-4-bromo-3-isoxazolyloxyacetamide,
N-(2-nitroxyethyl)-3-isoxazolyloxyacetamide,
N-(2-nitroxyethyl)-5-phenyl-4-bromo-3-isoxazolyloxyacetamide:
N-(2-nitroxyethyl)-4-bromo-3-isoxazolyloxyacetamide,
N-(2-nitroxyethyl)-4-chloro-3-isoxazolyloxyacetamide and
N-(2-nitroxyethyl)-1,4-benzodioxane-2-carboxamide.

33. A process for preparing a nitroxyalkylamide compound having the formula:

$$R^1-(A)_n-CONH-B'-ONO_2 \quad (I)$$

wherein A is a $C_1$–$C_4$ alkylene group,

B' is a $C_1$–$C_4$ alkylene group, n is 0 or 1, and $R^1$ represents a 5- or 6-membered heterocyclic group, which is unsubstituted or substituted or optionally condensed with a phenyl ring, containing from 1 to 3 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$–$C_{10}$ aryloxy group; or an optionally substituted $C_6$–$C_{10}$ arylthio group, the substituents being selected from the group consisting of a $C_1$–$C_4$ alkyl group, with a $C_1$–$C_4$ alkoxy group, a phenyl group optionally substituted with a $C_1$–$C_4$ alkyl group, with a $C_1$–$C_4$ alkoxy group or with a halogen atom; a halogen atom; a hydroxy group; an amino group; a mono-$C_1$–$C_4$ alkylamino group; a di-$C_1$–$C_4$ alkylamino group; and a nitro group; provided that, when n is 0, $R^1$ represents a 5- or 6-membered heterocyclic group, which is unsubstituted or substituted or optionally condensed with a phenyl ring, containing from 1 to 2 hetero-atoms selected from the group consisting of oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$–$C_{10}$ aryloxy group; or an optionally substituted $C_6$–$C_{10}$ arylthio group, or a pharmaceutically acceptable salt thereof, comprising reacting a compound having the formula:

$$R^1a-(A)_n-CO_2H \quad (II)$$

wherein $R^1a$ represents a 5- or 6-membered heterocyclic group, which is unsubstituted or substituted or optionally condensed with a phenyl ring, containing from 1 to 3 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$–$C_{10}$ aryloxy group; or an optionally substituted $C_6$–$C_{10}$ arylthio group, the substituents being selected from the group consisting of a $C_1$–$C_4$ alkyl group, a $C_1$–$C_4$ alkoxy group, a phenyl group optionally substituted with a $C_1$–$C_4$ alkyl group, with a $C_1$–$C_4$ alkoxy group or with a halogen atom; a halogen atom; a hydroxy group; an optionally protected amino group; an optionally protected mono-$C_1$–$C_4$ alkylamino group; a di-$C_1$–$C_4$ alkylamino group; and a nitro group; provided that, when n is 0, $R^1$ represents a 5- or 6-membered heterocyclic group, which is unsubstituted or substituted or optionally condensed with a phenyl ring, containing from 1 to 2 hetero-atoms selected from the group consisting of oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$–$C_{10}$ aryloxy group; or an optionally substituted $C_6$–$C_{10}$ arylthio group;

with a compound having the formula:

$$H_2N-B'-ONO_2 \quad (III)$$

and, optionally, removing an amino-($C_1$–$C_4$) alkylamino-protecting group or a mono-($C_1$–$C_4$) alkylamino-protecting group.

34. A process for preparing a compound according to claim 33 in which $R^1$ is a 5- or 6-membered heterocyclic group, which is unsubstituted or substituted or optionally condensed with a phenyl ring, containing from 1 to 2 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 2 hetero-atoms selected from the group consisting of nitrogen, oxygen and sulfur atoms; an optionally substituted phenoxy group or an optionally substituted phenylthio group, the substituents being selected from the group consisting of a $C_1$–$C_4$ alkyl group, a $C_1$–$C_2$ alkoxy group, a phenyl group; a halogen atom; a di-$C_1$–$C_2$ alkylamino group; and a nitro group.

35. A process for preparing a compound according to claim 33 in which A is a $C_1$–$C_2$ alkylene group.

36. A process for preparing a compound according to claim 33 in which B' is a $C_2$–$C_3$ alkylene group.

37. A process for preparing a compound according to claim 33 in which $R^1$ is a 5- or 6-membered heterocyclic group, which is unsubstituted or substituted or optionally condensed with a phenyl ring, containing from 1 to 2 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 2 hereto-atoms selected from the group consisting of nitrogen, oxygen and sulfur atoms; an optionally substituted phenoxy group or an optionally substituted phenylthio group, the substituents being selected from the group consisting of a $C_1$–$C_4$ alkyl group, a $C_1$–$C_2$ alkoxy group, a phenyl group; a halogen atom; a di-$C_1$–$C_2$ alkylamino group; and a nitro group; A is a $C_1$–$C_2$ alkylene group; and B' is a $C_2$–$C_3$ alkylene group.

38. A process for preparing a compound according to claim 33 in which $R^1$ is an optionally substituted furyl, furyloxy, thienyl, thienyloxy, isoxazolyl, isoxazolyloxy, phenoxy, phenylthio or 1,4-dibenzodioxanyl group, the substituents are selected from the group consisting of a $C_1$–$C_2$ alkyl group, phenyl, fluorine, chlorine, bromine, dimethylamino and nitro groups.

39. A process for preparing a compound according to claim 33 in which A is a methylene or methylmethylene group.

40. A process for preparing a compound according to claim 33 in which B' is an ethylene group.

41. A process for preparing a compound according to claim 33 in which $R^1$ is an optionally substituted furyl, furyloxy, thienyl, thienyloxy, isoxazolyl, isoxazolyloxy, phenoxy, phenylthio or 1,4-dibenzodioxanyl group, the substituents being selected from the group consisting of a $C_1$–$C_2$ alkyl group, phenyl, fluorine, chlorine, bromine, dimethylamino and nitro groups); A is a methylene or methylmethylene group; and B is an ethylene group.

42. A process for preparing a compound according to claim 33 in which $R^1$ is a phenoxy group and n is 0; or $R^1$ is a phenoxy group, a chlorophenoxy group, an optionally substituted isoxazol-3-yloxy group the substituents being selected from the group consisting of methyl, phenyl, chlorine and bromine or a 1,4-benzodioxanyl group, n is 1 and A is a methylene or methylmethylene.

43. A process for preparing a compound according to claim 33 in which $R^1$ is a phenoxy group and n is 0; or $R^1$ is a phenoxy group, a chlorophenoxy group, an optionally substituted isoxazol-3-yloxy group, the substituents being selected from the group consisting of methyl, phenyl, chlorine and bromine, or a 1,4-benzodioxanyl group, n is 1, A is a methylene or methylmethylene and B' is an ethylene group.

44. A process for preparing a compound according to claim 33 in which the compound (I) is phenyl N-(2-nitroxyethyl)carbamate.

45. A process for preparing a compound according to claim 33 in which the compound (I) is N-(2-nitroxyethyl)phenoxyacetamide.

46. A process for preparing a compound according to claim 33 in which the compound (I) is N-(2-nitroxyethyl)-2-chlorophenoxyacetamide.

47. A process for preparing a compound according to claim 33 in which the compound (I) is N-(2-nitroxyethyl)-2-phenoxypropanamide.

48. A process for preparing a compound according to claim 33 in which the compound (I) is N-(2-nitroxyethyl)-5-methyl-4-chloro-3-isoxazolyloxyacetamide.

49. A process for preparing a compound according to claim 33 in which the compound (I) is N-(2-nitroxyethyl)-5-phenyl-3-isoxazolyloxyacetamide.

50. A process for preparing a compound according to claim 33 in which the compound (I) is N-(2-nitroxyethyl)-5-methyl-3-isoxazolyloxyacetamide.

51. A process for preparing a compound according to claim 33 in which the compound (I) is N-(2-nitroxyethyl)-5-methyl-4-bromo-3-isoxazolyloxyacetamide.

52. A process for preparing a compound according to claim 33 in which the compound (I) is N-(2-nitroxyethyl)-3-isoxazolyloxyacetamide.

53. A process for preparing a compound according to claim 33 in which the compound (I) is N-(2-nitroxyethyl)-5-phenyl-4-bromo-3-isoxazolyloxyacetamide.

54. A process for preparing a compound according to claim 33 in which the compound (I) is N-(2-nitroxyethyl)-4-bromo-3-isoxazolyloxyacetamide.

55. A process for preparing a compound according to claim 33 in which the compound (I) is N-(2-nitroxyethyl)-4-chloro-3-isoxazolyloxyacetamide.

56. A process for preparing a compound according to claim 33 in which the compound (I) is N-(2-nitroxyethyl)-1,4-benzodioxane-2-carboxamide.

57. A process for preparing a nitroxyalkylamide compound having the formula:

$$R^1-(A)_n-CONH-B'-ONO_2 \quad (I)$$

wherein A is a $C_1$–$C_4$ alkylene group, n is 0 or 1,

B' is a $C_1$–$C_4$ alkylene group, and $R^1$ is a 5- or 6-membered heterocyclic group, which is unsubstituted or substituted or optionally condensed with a phenyl ring, containing from 1 to 3 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$–$C_{10}$ aryloxy group; or an optionally substituted $C_6$–$C_{10}$ arylthio group, the substituents being selected from the group consisting of a $C_1$–$C_4$ alkyl group, a $C_1$–$C_4$ alkoxy group, a phenyl group optionally substituted with a $C_1$–$C_4$ alkyl group, with a $C_1$–$C_4$ alkoxy group or with at least one halogen atom; a halogen atom; a hydroxy group, an amino group; a mono-$C_1$-$C_4$ alkylamino group, a di-$C_1$-$C_4$ alkylamino group; and a nitro group; or a pharmaceutically acceptable salt thereof, comprising reacting a compound having the formula:

$$R^1a\text{—}(A)_n\text{—}CO_2H \qquad (II)$$

wherein $R^1a$ represents a 5- or 6-membered heterocyclic group, which is unsubstituted or substituted or optionally condensed with a phenyl ring, containing from 1 to 3 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$-$C_{10}$ aryloxy group; or an optionally substituted $C_6$-$C_{10}$ arylthio group, the substituents being selected from the group consisting of a $C_1$-$C_4$ alkyl group, a $C_1$-$C_4$ alkoxy group, a phenyl group optionally substituted with a $C_1$-$C_4$ alkyl group, with a $C_1$-$C_4$ alkoxy group or with a halogen atom; a halogen atom; a hydroxy group; an optionally protected amino group; an optionally protected mono-$C_1$-$C_4$ alkylamino group; a di-$C_1$-$C_4$ alkylamino group; and a nitro group; provided that, when n is 0, $R^1$ represents a 5- or 6-membered heterocyclic group, which is unsubstituted or substituted or optionally condensed with a phenyl ring, containing from 1 to 2 hetero-atoms selected from the group consisting of oxygen and sulfur atoms; a 5- or 6membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$-$C_{10}$ aryloxy group; or an optionally substituted $C_6$-$C_{10}$ arylthio group;

with a compound having the formula:

$$H_2N\text{—}B'\text{—}OH \qquad (IV)$$

and, optionally, removing an amino-($C_1$-$C_4$) alkylamino protecting group or a mono-($C_1$-$C_4$) alkylamino-protecting group, to prepare a compound having the formula:

$$R^1\text{—}(A)_n\text{—}CONH\text{—}B'\text{—}OH \qquad (V)$$

provided that, when n is 0, $R^1$ represents a 5- or 6-membered heterocyclic group, which is unsubstituted or substituted or optionally condensed with a phenyl ring, containing from 1 to 2 hetero-atoms selected from the group consisting of oxygen and sulfur atoms; a 5- or 6-membered heterocyclic-oxy group, which is unsubstituted or substituted or optionally condensed with a phenyl ring, containing from 1 to 3 hetero-atoms selected from the group consisting of nitrogen, oxygen and sulfur atoms; an optionally substituted $C_6$-$C_{10}$ aryloxy group; or an optionally substituted $C_6$-$C_{10}$ arylthio group; and then reacting the resulting compound (V) with a nitrating agent.

58. A process for preparing a compound according to claim 57 in which $R^1$ is a 5- or 6-membered heterocyclic group, which is unsubstituted or substituted or optionally condensed with a phenyl ring, containing from 1 to 2 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 2 hetero-atoms selected from the group consisting of nitrogen, oxygen and sulfur atoms; an optionally substituted phenoxy group or an optionally substituted phenylthio group, the substituents being selected from the group consisting of a $C_1$-$C_4$ alkyl group, a $C_1$-$C_2$ alkoxy group, a phenyl group; a halogen atom; a di-$C_1$-$C_2$ alkylamino group; and a nitro group.

59. A process for preparing a compound according to claim 57 in which A is a $C_1$-$C_2$ alkylene group.

60. A process for preparing a compound according to claim 57 in which B' is a $C_2$-$C_3$ alkylene group.

61. A process for preparing a compound according to claim 57 in which $R^1$ is a 5- or 6-membered heterocyclic group, which is unsubstituted or substituted or optionally condensed with a phenyl ring, containing from 1 to 2 hetero-atoms selected from the group consisting of nitrogen, oxygen and sulfur atoms; a 5- or 6-membered heterocyclic-oxy group, which is unsubstituted or substituted or optionally condensed with a phenyl ring, containing from 1 to 2 heteroatoms selected from the group consisting of nitrogen, oxygen and sulfur atoms; an optionally substituted phenoxy group or an optionally substituted phenylthio group, the substituents being selected from the group consisting of a $C_1$-$C_4$ alkyl group, a $C_1$-$C_2$ alkoxy group, a phenyl group; a halogen atom; a di-$C_1$-$C_2$ alkylamino group; and a nitro group; A is a $C_1$-$C_2$ alkylene group; and B' is a $C_2$-$C_3$ alkylene group.

62. A process for preparing a compound according to claim 57 in which $R^1$ is an optionally substituted furyl, furyloxy, thienyl, thienyloxy, isoxazolyl, isoxazolyloxy, phenoxy, phenylthio or 1,4-dibenzodioxanyl group, the substituents being selected from the group consisting of a $C_1$-$C_2$ alkyl group, phenyl, fluorine, chlorine, bromine, dimethylamino and nitro groups.

63. A process for preparing a compound according to claim 57 in which A is a methylene or methylmethylene group.

64. A process for preparing a compound according to claim 57 in which B' is an ethylene group.

65. A process for preparing a compound according to claim 57 in which $R^1$ is an optionally substituted furyl, furyloxy, thienyl, thienyloxy, isoxazolyl, isoxazolyloxy, phenoxy, phenylthio or 1,4-dibenzodioxanyl group, the substituents being selected from the group consisting of a $C_1$-$C_2$ alkyl group, phenyl, fluorine, chlorine, bromine, dimethylamino and nitro group; A is a methylene or methylmethylene group; and B is an ethylene group.

66. A process for preparing a compound according to claim 57 in which $R^1$ is a phenoxy group and n is 0; or $R^1$ is a phenoxy group, a chlorophenoxy group, an optionally substituted isoxazol-3-yloxy group, the substituents being selected from the group consisting of methyl, phenyl, chlorine and bromine, or a 1,4-benzodioxanyl group, n is 1 and A is a methylene or methylmethylene.

67. A process for preparing a compound according to claim 57 in which $R^1$ is a phenoxy group and n is 0; or $R^1$ is a phenoxy group, a chlorophenoxy group, or an optionally substituted isoxazol-3-yloxy group, the substituents being selected from the group consisting of methyl, phenyl, chlorine and bromine, or a 1,4-benzodioxanyl group, n is 1, A is a methylene or methylmethylene group and B' is an ethylene group.

68. A process for preparing a compound according to claim 57 in which the compound (I) is phenyl N-(2-nitroxyethyl)carbamate.

69. A process for preparing a compound according to claim 57 in which the compound (I) is N-(2-nitroxyethyl)phenoxyacetamide.

70. A process for preparing a compound according to claim 57 in which the compound (I) is N-(2-nitroxyethyl)-2-chlorophenoxyacetamide.

71. A process for preparing a compound according to claim 57 in which the compound (I) is N-(2-nitroxyethyl)-2-phenoxypropanamide.

72. A process for preparing a compound according to claim 57 in which the compound (I) is N-(2-nitroxyethyl)-5-methyl-4-chloro-3-isoxazolyloxyacetamide.

73. A process for preparing a compound according to claim 57 in which the compound (I) is N-(2-nitroxyethyl)-5-phenyl-3-isoxazolyloxyacetamide.

74. A process for preparing a compound according to claim 57 in which the compound (I) is N-(2-nitroxyethyl)-5-methyl-3-isoxazolyloxyacetamide.

75. A process for preparing a compound according to claim 57 in which the compound (I) is N-(2-nitroxyethyl)-5-methyl-4-bromo-3-isoxazolyloxyacetamide.

76. A process for preparing a compound according to claim 57 in which the compound (I) is N-(2-nitroxyethyl)-3-isoxazolyloxyacetamide.

77. A process for preparing a compound according to claim 57 in which the compound (I) is N-(2-nitroxyethyl)-5-phenyl-4-bromo-3-isoxazolyloxyacetamide.

78. A process for preparing a compound according to claim 57 in which the compound (I) is N-(2-nitroxyethyl)-4-bromo-3-isoxazolyloxyacetamide.

79. A process for preparing a compound according to claim 57 in which the compound (I) is N-(2-nitroxyethyl)-4-chloro-3-isoxazolyloxyacetamide.

80. A process for preparing a compound according to claim 57 in which the compound (I) is N-(2-nitroxyethyl)-1,4-benzodioxane-2-carboxamide.

* * * * *

UNITED STATES PATENT AND TRADEMARK OFFICE
CERTIFICATE OF CORRECTION

PATENT NO.  : 5,580,893
DATED       : December 3, 1996
INVENTOR(S) : ISHIHARA et al It is certified that error appears in the above-identified patent and that said Letters Patent is hereby corrected as shown below:

Column 21, (Claim 42) line 62:  after "group" insert --,--;

line 64:  after "bromine" insert --,--;

Signed and Sealed this

Fifth Day of January, 1999

Attest:

Attesting Officer

*Acting Commissioner of Patents and Trademarks*